US012478510B2

(12) United States Patent
Ganzoni

(10) Patent No.: US 12,478,510 B2
(45) Date of Patent: Nov. 25, 2025

(54) MEDICAL COMPRESSION GARMENT WITH A SPECIAL JOINT SECTION FOR INCREASED RANGE OF MOTION

(71) Applicant: SIGVARIS AG, St. Gallen (CH)

(72) Inventor: Levin Andreas Ganzoni, Zurich (CH)

(73) Assignee: SIGVARIS AG, St. Gallen (CH)

( * ) Notice: Subject to any disclaimer, the term of this patent is extended or adjusted under 35 U.S.C. 154(b) by 339 days.

(21) Appl. No.: 17/630,618

(22) PCT Filed: Jul. 13, 2020

(86) PCT No.: PCT/EP2020/069750
§ 371 (c)(1),
(2) Date: Jan. 27, 2022

(87) PCT Pub. No.: WO2021/032361
PCT Pub. Date: Feb. 25, 2021

(65) Prior Publication Data

US 2022/0265480 A1 Aug. 25, 2022

(30) Foreign Application Priority Data

Aug. 19, 2019 (CH) .................................... 01039/19

(51) Int. Cl.
*A61F 13/02* (2024.01)
*A61F 13/00* (2024.01)
(Continued)

(52) U.S. Cl.
CPC ...... *A61F 13/0273* (2013.01); *A61F 13/0008* (2013.01); *A61F 13/01029* (2024.01);
(Continued)

(58) Field of Classification Search
CPC ................ A61F 13/00; A61F 13/00004; A61F 13/00119; A61F 13/0273; A61F 13/01029;
(Continued)

(56) References Cited

U.S. PATENT DOCUMENTS 3,004,868 A * 10/1961 Sumner .................. D04H 1/587 442/107
3,842,832 A * 10/1974 Wideman .................. B32B 7/12 428/179
(Continued)

FOREIGN PATENT DOCUMENTS

CH 712938 A1 * 3/2018 ....... A61F 13/00038
DE 4129675 C1 * 4/1993 ........... A61F 13/107
(Continued)

OTHER PUBLICATIONS

CH 712938 A1 machine translation (Year: 2018).*
(Continued)

*Primary Examiner* — Caitlin A Carreiro
(74) *Attorney, Agent, or Firm* — FisherBroyles LLP; Anthony J DoVale

(57) ABSTRACT

A medical compression garment for applying compression to a patient's body part may include a first material adapted to be wrapped around the body part, and a second material fixated on a section of the first material. The second material collapses the first material such that the first material forms wrinkles along the section.

14 Claims, 2 Drawing Sheets

(51) Int. Cl.
*A61F 13/01* (2024.01)
*A61F 13/08* (2006.01)
*A61F 13/10* (2006.01)

(52) U.S. Cl.
CPC ...... *A61F 13/01038* (2024.01); *A61F 13/085* (2013.01); *A61F 13/107* (2013.01)

(58) Field of Classification Search
CPC .... A61F 13/01038; A61F 13/08; A61F 13/10; A61F 13/085; A61F 13/107; A61F 13/0008; A61F 13/0286; A61F 13/01008; A61F 5/01; A61F 15/006; A41B 11/00
USPC ................ 602/41, 53, 60, 75, 78; 2/239, 16; 450/7, 11, 28, 29
See application file for complete search history.

(56) References Cited

U.S. PATENT DOCUMENTS

| | | | | |
|---|---|---|---|---|
| 4,653,442 | A * | 3/1987 | Swenson | ............ F02N 11/0803 290/37 A |
| 4,653,492 | A | 3/1987 | Parsons | |
| 2017/0105877 | A1* | 4/2017 | Buteux | ................ A61F 13/068 |

FOREIGN PATENT DOCUMENTS

| | | | | |
|---|---|---|---|---|
| DE | 3718076 | C2 * | 10/2000 | ......... A61F 13/4752 |
| KR | 1999-0083740 | A | 12/1999 | |
| WO | 95/16416 | A1 | 6/1995 | |
| WO | WO-2009004282 | A2 * | 1/2009 | ....... A61F 13/00063 |

OTHER PUBLICATIONS

DE 4129675 C1 machine translation (Year: 1993).*
DE 3718076 C2 machine translation (Year: 2000).*
Sigvaris AG, Application No. PCT/EP2020/069750; International Search Report; ISA/EP; Sep. 22, 2020; 3 pp.
Sigvaris AG, Application No. PCT/EP2020/069750; Written Opinion; ISA/EP; Sep. 22, 2020; 5 pp.

* cited by examiner

MEDICAL COMPRESSION GARMENT WITH A SPECIAL JOINT SECTION FOR INCREASED RANGE OF MOTION

TECHNICAL FIELD

The present invention relates to a medical compression garment for applying compression to a patient's body part comprising a first material adapted to be wrapped around the body part and a second material fixated on a section of the first material. Furthermore, the present invention relates to a method for producing such a medical compression garment.

BACKGROUND ART

Medical compression garments are used to provide a pressure or a compressive force, respectively, to a human body part, especially to a limb such as an arm or a leg for e.g. the treatment of venous diseases and lymphatic disorders.

Medical compression garments limit the range of motion of the human extremities, especially the joint movement since many medical compression garments comprise almost inelastic materials.

DISCLOSURE OF THE INVENTION

The object of the present invention is to provide a medical compression garment that restricts the range of motion of compressed body parts as little as possible.

In order to meet this object, a first aspect of the invention introduces a medical compression garment according to claim 1.

The medical compression garment for applying compression to a patient's body part comprises

- a first material adapted to be wrapped around the body part, and
- a second material fixated on a section of the first material. The second material collapses the first material such that the first material forms wrinkles along the section.

This has the advantage that the first material forms wrinkles in a controlled manner. Uncontrolled wrinkles, which are uncomfortable, are avoided. If the wrinkles are located at a joint, e.g. at an elbow, the range of motion of the joint and the wearing comfort are improved.

Advantageously, the second material is more elastic than the first material, in particular wherein the stretchability of the second material is twice as high, in particular five times as high, as the stretchability of the first material.

The high stretchability of the second material allows the forming of the wrinkles and ensures a good fit around the joint.

In a preferred embodiment, the stretchability of the first material is increased by the wrinkles in the direction perpendicular to the wrinkles. This improves the wearing comfort and makes the donning of the garment very easy.

Furthermore, the wrinkles can be arranged at a joint part, in particular at an elbow part, of the medical compression garment. The joint part of a medical compression garment is the part which is shaped for positioning on the human joint.

Advantageously, the second material extends in longitudinal direction such that the first material forms at least three, in particular at least five, in particular at least eight, in particular at least ten, wrinkles. Only a sufficiently large number of wrinkles allows comfortable wearing at the joint.

In particular, the second material is attached to the first material by gluing, welding, or sewing, in particular between every wrinkle. This results in a robust compression garment, which can be worn for a long time.

In a preferred embodiment, the second material extends over a fraction of the width or the full width of the first material.

In particular, the first material is a textile or leather or plastic or laminated foam.

Preferably, the second material is a textile or foil or plastic or laminated foam.

Advantageously, the first material comprises at least one closing part for fixating the wrapped first material around the body part.

Furthermore, an object of the present invention is to provide a method for producing the inventive medical compression garment.

The method for producing a medical compression garment comprises the following steps:

- fixating the first material in a fixation device in a relaxed state,
- arranging the second material in a stretched state onto the first material in the fixation device,
- attaching, in particular sewing, the first material to the second material,
- removing the fixation device such that the second material relaxes and that the first material forms wrinkles.

BRIEF DESCRIPTION OF THE DRAWINGS

The above and other features and advantages of the present invention will become more apparent to those of ordinary skill in the art by describing in detail preferred embodiments thereof with reference to the attached drawings in which.

MODES FOR CARRYING OUT THE INVENTION

Figure 1:
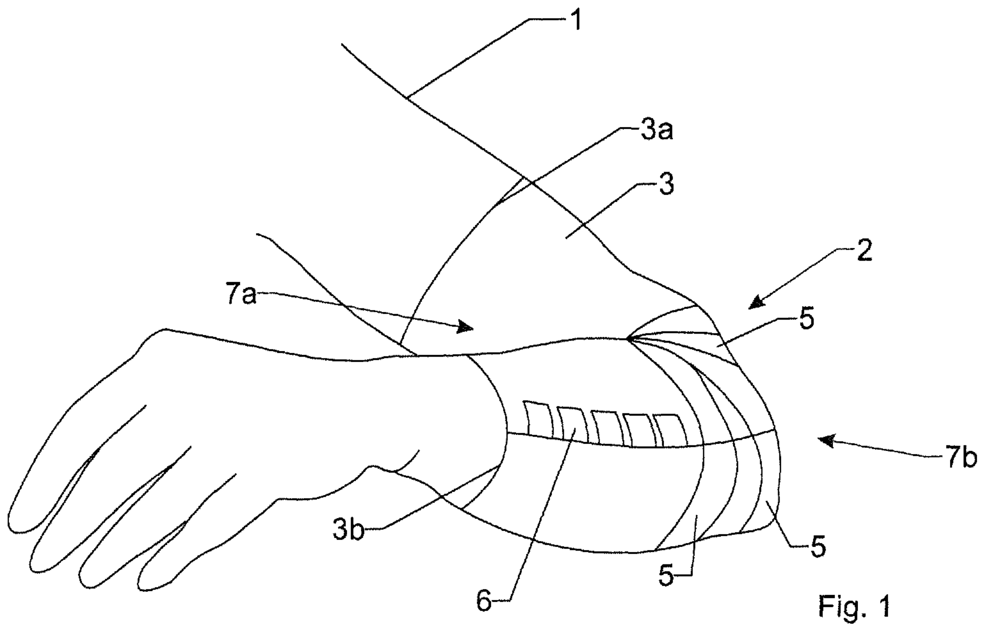
FIG. 1 illustrates an example embodiment of the disclosed medical compression garment applied at an arm.

FIG. 1 shows a human arm 1 with an elbow. A medical compression garment 2 is applied to the arm. The medical compression garment comprises a first material 3 which extends from a first end 3*a* to a second end 3*b*. The first material 3 extends over the full length of the medical compression garment 2. A second material 4 is fixated in a middle section of the medical compression garment 2. The second material 4 is not visible in FIG. 1 since it is arranged on the inner side of the medical compression garment, i.e. it touches the surface of the arm 1. But the second material 4 collapses the first material 3 such that the first material forms wrinkles 5 along the section where the second material 4 is fixated. The wrinkles 5 are visible in FIG. 1.

With other words, the wrinkles 5 are present regardless of whether the arm is straight or bent. When the arm is bent, the wrinkles 5 are already formed and defined such that no new wrinkles are formed on the inner side 7*a* of the elbow which would press uncomfortably hard on the elbow joint. On the outer side 7*b* of the elbow, the preformed wrinkles 5 are stretched, such that the medical compression garment lies comfortably on the elbow.

The medical compression garment 2 is a garment which is wrapped around the arm and fixated by closing parts 6.

Figure 2:
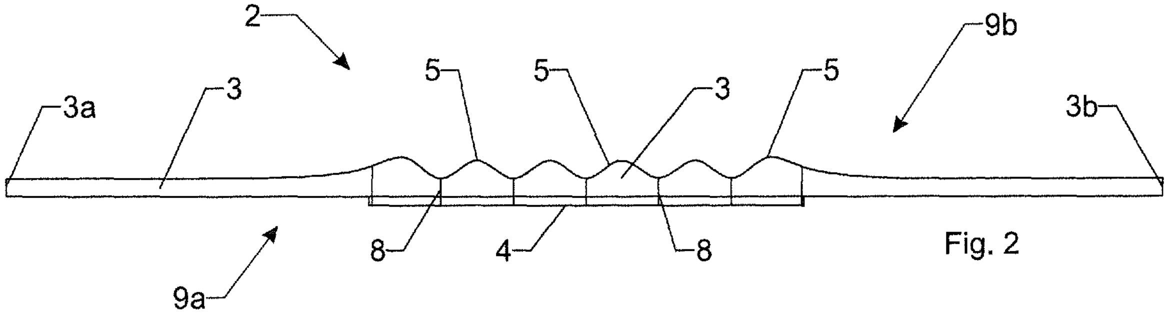
FIG. 2 is a sectional view of the medical compression garment in a relaxed state showing the wrinkles of the first material.

FIG. 2 shows a sectional view of the medical compression garment 2 along its length axis. The medical compression garment 2 comprises a first material 3, which extends from the first end 3*a* to the second end 3*b*, and a second material 4 which is arranged in the middle section of the medical compression garment 2.

The first material 3 and the second material 4 are attached to each other by seams 8 between every wrinkle 5. The second material 4 is more elastic than the first material 3. Since the second material 4 is seamed to the first material 3 in a stretched state, it collapses the first material 3 in a relaxed state and six wrinkles 5 are formed. The section where the second material 4 is attached to the first material 3 is called the joint part or the elbow part of the medical compression garment, since this part is intended to be placed at the human elbow.

In the present embodiment, the inner side 9*a* of the medical compression garment, where the second material 4 is attached, is intended to touch the skin of the human. The outer side 9*b* lies on the opposite side of the inner side 9*a*. It does not touch the skin of the human body and is adapted such that the closing parts 6 can be attached to the outer side.

In the present embodiment, the first material 3 is a textile, in particular a spacer fabric, and the second material 4 is also a textile, but it is more elastic than the textile of the first material 3.

Figure 3:
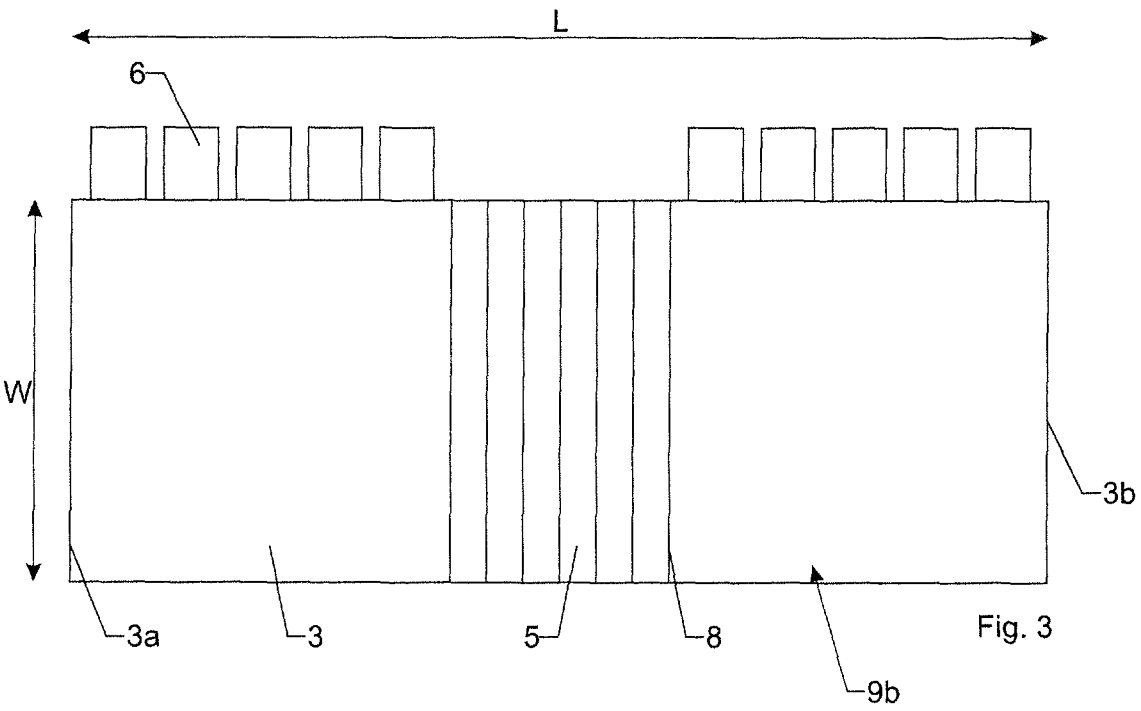
FIG. 3 shows a medical compression garment in an unwrapped state.

FIG. 3 shows the medical compression garment from a top view in an unwrapped state. The first material 3 extends over the full length L and the second material (not shown in FIG. 3) is attached to the first material 3 such that wrinkles 5 are formed over the full width W in the middle part of the medical compression garment 2. The medical compression garment 2 is wrapped around the body part and fixated by the closing parts 6.

Furthermore, the second material 4 can be attached to the first material 3 such that the stretchability of the first material 3 is increased in the direction perpendicular to the wrinkles 5, i.e. perpendicular to the direction of the width W.

Figure 4A:
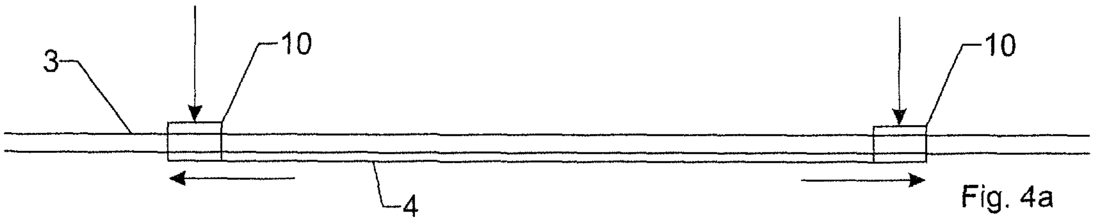
FIGS. 4*a*, 4*b* and 4*c* show the method of producing the disclosed medical compression garment.
Figure 4B:
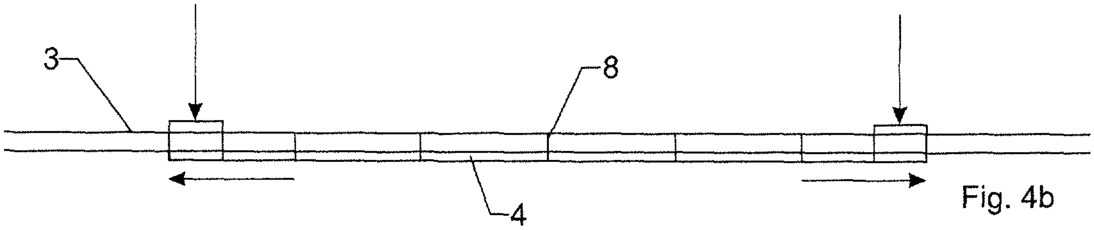
Figure 4C:
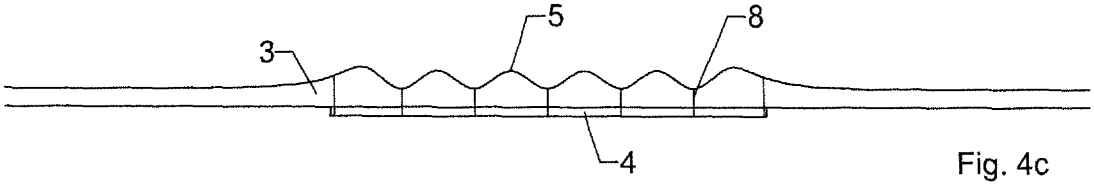

The FIGS. 4*a*, 4*b* and 4*c* illustrate the method for producing the medical compression garment. The method comprises the following steps:

- the first material 3 is fixated in a fixation device 10 in a relaxed state (FIG. 4*a*);
- the second material 4 is arranged in a stretched state onto the first material 3 and fixated in the fixation device 10 (FIG. 4*a*);
- the first material 3 is attached to the second material 4 by sewing the first material 3 and the second material 4 together (FIG. 4*b*);
- the fixation device 10 is removed such that the second material 4 relaxes and that the first material 3 forms wrinkles 5.

The present invention has so far been described for some specific embodiments shown in the figures. It must be noted that it also can be practiced differently.

The invention claimed is:

1. A medical compression garment for applying compression to an arm of a patient comprising:

- at least one closing part along a longitudinal side of the medical compression garment for fixating the medical compression garment around the arm as to form a sleeve when fixated on the arm;
- a first material adapted to be wrapped around the whole circumference of the arm;
- a second material fixated on a section of the first material and over the full width of the first material, wherein the second material collapses the first material and over the full width of the first material such that the first material forms wrinkles exclusively at an elbow part of the medical compression garment, wherein the wrinkles extend over the full width of the first material, perpendicular to a longitudinal direction of the medical compression garment; and
- wherein the second material is more elastic than the first material and the second material is configured to be positioned substantially adjacent to and in contact with the arm of the patient when the compression garment is fixated around the arm of the patient.

2. The medical compression garment according to claim 1, wherein the second material extends in the longitudinal direction such that the first material forms at least three wrinkles.

3. The medical compression garment according to claim 2, wherein the second material extends in the longitudinal direction such that the first material forms at least five wrinkles.

4. The medical compression garment according to claim 2, wherein the second material extends in the longitudinal direction such that the first material forms at least eight wrinkles.

5. The medical compression garment according to claim 2, wherein the second material extends in the longitudinal direction such that the first material forms at least ten wrinkles.

6. The medical compression garment according to claim 1, wherein a stretchability of the first material is increased by the wrinkles in a direction perpendicular to the wrinkles.

7. The medical compression garment according to claim 1, wherein the second material is attached to the first material by gluing, welding, or sewing.

8. The medical compression garment according to claim 1, wherein the first material is a textile or leather or plastic or laminated foam.

9. The medical compression garment according to claim 1, wherein the second material is a textile or foil or plastic or laminated foam.

10. The medical compression garment of claim 1, wherein a stretchability of the second material is at least twice as high as a stretchability of the first material.

11. The medical compression garment of claim 1, wherein a stretchability of the second material is at least five times as high as a stretchability of the first material.

12. The medical compression garment according to claim 1, wherein the second material is attached to the first material between adjacent wrinkles by gluing, welding, or sewing.

13. The medical compression garment according to claim 1, further comprising a first section and a second section and an elbow section comprising the elbow part, wherein the first material extends in the longitudinal direction from a first end to a second end, the first section being at the first end and the second section being at the second end and the elbow section being between the first section and the second section.

14. A method for producing a medical compression garment according to claim 1 with the following steps:

- fixating the first material in a fixation device in a relaxed state,
- arranging the second material in a stretched state onto the first material in the fixation device, attaching the first material to the second material,
removing the fixation device such that the second material relaxes and the first material forms wrinkles.

* * * * *